United States Patent
Hwang et al.

(10) Patent No.: US 9,155,715 B2
(45) Date of Patent: Oct. 13, 2015

(54) TRANSDERMAL COMPOSITION COMPRISING TOLTERODINE

(75) Inventors: Yong Youn Hwang, Suwon-si (KR); Won Jae Choi, Seoul (KR); Yeo-Jin Park, Seoul (KR); Joon-gyo Oh, Suwon-si (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/381,328

(22) PCT Filed: May 27, 2010

(86) PCT No.: PCT/KR2010/003365
§ 371 (c)(1),
(2), (4) Date: Jan. 25, 2012

(87) PCT Pub. No.: WO2011/002161
PCT Pub. Date: Jan. 6, 2011

(65) Prior Publication Data
US 2012/0123162 A1     May 17, 2012

(30) Foreign Application Priority Data

Jun. 29, 2009 (KR) .......................... 10-2009-0058499

(51) Int. Cl.
| C07C 211/00 | (2006.01) |
| A61L 15/16 | (2006.01) |
| A61K 31/137 | (2006.01) |
| A61K 9/06 | (2006.01) |
| A61K 9/70 | (2006.01) |
| A61K 47/12 | (2006.01) |
| A61K 47/18 | (2006.01) |
| A61K 47/20 | (2006.01) |
| A61K 47/38 | (2006.01) |

(52) U.S. Cl.
CPC ................. *A61K 31/137* (2013.01); *A61K 9/06* (2013.01); *A61K 9/7061* (2013.01); *A61K 47/12* (2013.01); *A61K 47/183* (2013.01); *A61K 47/20* (2013.01); *A61K 47/38* (2013.01)

(58) Field of Classification Search
None
See application file for complete search history.

(56) References Cited

U.S. PATENT DOCUMENTS

| 5,382,600 | A | 1/1995 | Jonsson et al. | |
| 6,517,864 | B1 | 2/2003 | Orup Jacobsen et al. | |
| 6,783,769 | B1 | 8/2004 | Arth et al. | |
| 2005/0287194 | A1 | 12/2005 | Grenier et al. | |
| 2009/0202634 | A1* | 8/2009 | Jans et al. | 424/468 |
| 2010/0239667 | A1* | 9/2010 | Hemmingsen et al. | 424/466 |

FOREIGN PATENT DOCUMENTS

WO    WO 98/03067    1/1998

OTHER PUBLICATIONS

Zhao, Ligang et al.: "Transdermal delivery of tolterodine by O-acylmenthol: In vitro/in vivo correlation", *International Journal of Pharmaceutics*, 374 (2009), pp. 73-81.

* cited by examiner

*Primary Examiner* — Clinton Brooks
(74) *Attorney, Agent, or Firm* — Frommer Lawrence & Haug LLP

(57) ABSTRACT

A transdermal composition comprising tolterodine having improved storage stability is disclosed. The transdermal composition comprising tolterodine contains an antioxidant to stabilize tolterodine and can be stored for a long period of time.

14 Claims, No Drawings

TRANSDERMAL COMPOSITION COMPRISING TOLTERODINE

This application is a 371 of PCT/KR2010/003365 filed on May 27, 2010 published on Jan. 6, 2011 under publication number WO 2011/002161 A which claims priority benefits to Korean Patent Application Number 10-2009-0058499 filed Jun. 29, 2009, the disclosure of which is incorporated herein by reference.

TECHNICAL FIELD

The present invention relates to a transdermal composition comprising tolterodine having improved storage stability.

BACKGROUND ART

Overactive bladder is a urological condition defined by a set of symptoms such as urinary frequency, urinary urgency, and urge incontinence. Urinary frequency refers to a condition in which people urinate more than 8 times a day. The urge to urinate may remain even after urination. Urinary urgency refers to a sudden strong urge to urinate with little or no chance to postpone the urination. Urge incontinence refers to an involuntary loss of urine associated with urinary urgency. It is estimated that more than 50 million have overactive bladder globally and it occurs in 22% of people aged 40 or older. Although overactive bladder occurs in both sexes of all ages, it is more frequent in women. It is often associated with frequent contraction of detrusor, the smooth muscle of the bladder. That is, because the bladder muscle contracts more frequently than normal or necessary, the patient feels a sudden, compelling urge to urinate although the bladder is not full. The causes are mostly unknown. In some patients, signaling from the brain to the bladder may be problematic. Damage to the nerves caused by surgical operation or childbirth may also be the cause. Some male patients have the overactive bladder disease along with prostatic hyperplasia.

Overactive bladder significantly affects quality of life by leading to lack of sleep, decreased work efficiency, avoidance of sex, depression and avoidance of inter-personal relations caused by lack of knowledge about the disease and shame. According to a study about the quality of life (SF-36 questionnaire), overactive bladder has a worse effect on quality of life than chronic diseases such as diabetes and hypertension.

Accordingly, development of a novel pharmaceutical compound capable of improving the quality of life of individuals is required.

U.S. Pat. No. 5,382,600 discloses that (substituted) 3,3-diphenylpropylamine is useful in treating overactive bladder. Especially, the patent teaches that tolterodine, the N,N-diisopropyl-3-(2-hydroxy-5-methylphenyl)-3-phenylpropylamine compound having the formula 2-[(1R)-3-(diisopropylamino)-1-phenylpropyl)]-4-methylphenol is useful.

U.S. Pat. No. 6,517,864 discloses that transdermal administration of tolterodine is effective for treatment of overactive bladder. Particularly, this patent teaches that tolterodine is advantageous for transdermal administration because of high potency and short half-life and a more therapeutic effect on overactive bladder may be attained due to a more constant serum concentration.

Tolterodine is currently marketed as an orally administered drug under the trade name Detrol in the form of tartrate salt. Although a free base form of tolterodine is best suited for transdermal administration, it has decreased stability.

SUMMARY OF INVENTION

Technical Problem

The inventors of the present invention have made efforts to develop a new drug delivery system capable of ensuring pharmaceutical stability of tolterodine and improving quality of life of patients with improvement of compliance. As a result, they developed a transdermal composition comprising a specific antioxidant as a stabilizer and having superior stability and completed the present invention.

Accordingly, an object of the present invention is to provide a transdermal composition comprising tolterodine with superior stability.

Solution to Problem

To accomplish the aforesaid object, the present invention provides a transdermal composition comprising tolterodine, which contains an antioxidant as a stabilizer and can be stored for a long period of time.

Advantageous Effects of Invention

The composition for transdermal administration according to the present invention, which contains an antioxidant as a stabilizer, can be stored for a long period of time.

BEST MODE FOR CARRYING OUT THE INVENTION

Hereinafter, the embodiments of the present invention will be described in detail.

In order to understand why tolterodine is unstable, decomposition test was performed under stress conditions of acid, base, oxidation and heat. Much of decomposed substances of tolterodine were produced under a harsh oxidizing condition.

Thus, in order to ensure stability under a harsh oxidizing condition, an antioxidant that can ensure the stability of tolterodine and satisfy the processability of preparation into transdermal formulation is used. Preferably, the antioxidant is one or more selected from organic acids and derivatives thereof, amino acids and derivatives, and metal thiolates.

The organic acid as the antioxidant may be selected from, e.g., formic acid, fumaric acid, malic acid, succinic acid, acetic acid, palmitic acid, tartaric acid, ascorbic acid, uric acid, sulfonic acid, sulfinic acid, aspartic acid, citric acid, isocitric acid, α-ketoglutaric acid, glutamic acid, or the like. The amino acid as the antioxidant may be selected from, e.g., glutamine, asparagine, serine, threonine, tyrosine, cysteine and cystine. The organic acid derivative as the antioxidant may be selected from, e.g., sodium glutamate, an ascorbic acid derivative such as ascorbic acid 2-phosphate, ascorbic acid 2-glucoside, ascorbic acid 6-palmitate, ascorbic acid 2-phosphate-6-palmitate, ascorbic acid 2-phosphate-6-hexyldecanoate and ascorbic acid 2-phosphate-6-stearate, and salts thereof. The amino acid derivative as the antioxidant may be, e.g., cysteine hydrochloride.

And, the metal thiolate as the antioxidant may be, e.g., sodium thiosulfate, potassium thiosulfate, magnesium thiosulfate, or the like.

In the present invention, the antioxidant is used of 1 to 40 parts by weight, preferably 2 to 30 parts by weight, more preferably 5 to 25 parts by weight, most preferably 7 to 20 parts by weight, based on 100 parts by weight of tolterodine.

Tolterodine may be in any form, including a free base and an acid addition salt. A free base is preferred considering the transdermal absorption rate of the drug.

The transdermal composition according to the present invention may be prepared into such formulations as patch, liquid, ointment, gel, or the like according to a method commonly employed in the art. A patch form is preferred. In the present invention, various excipients aiding in transdermal absorption and adhesives aiding in adhesion to the skin may be used as a base of the patch.

A solvent used to dissolve the drug when preparing the patch may be ethyl acetate, ethanol, propylene glycol, or the like, and may be used of 50 to 500 parts by weight tolterodine 100 parts by weight.

An adhesive polymer that may be used to prepare the transdermal composition according to the present invention into a patch may be a water-based or organic solvent-based pressure sensitive adhesive (PSA) for medical use. Preferably, one or more of an acryl-based adhesive such as acrylate polymer, vinyl acetate-acrylate copolymer, a synthetic rubber such as polyisobutylene, polystyrene, polybutadiene or copolymers thereof, a natural rubber, a silicone-based adhesive, or the like. Preferably, the adhesive polymer is contained in an amount of 100 to 2000 parts by weight based on 100 parts by weight of tolterodine. If the adhesive polymer is used less than 100 parts by weight, the added components do not form a uniform phase, thereby resulting in difficulty application, nonuniform content, decreased adhesivity, or the like. Meanwhile, if it is used exceeding 2000 parts by weight, relative contents of the drug and other additives decrease, thereby leading to significantly decreased absorption of the drug.

The administration dose of the composition according to the present invention may vary depending on age, body weight, sex and physical conditions of the patient, administration route, severity of disease, or the like. An oral dosage of tolterodine for overactive bladder such as urinary frequency, urinary urgency and urge incontinence is 2 mg, twice a day.

MODE FOR THE INVENTION

The examples and experiments will now be described. The following examples and experiments are for illustrative purposes only and not intended to limit the scope of this invention.

Reference Example 1

Stress Decomposition Test of Tolterodine Under Acidic/Basic/Oxidizing Conditions Tolterodine free base (20 mg) was added respectively to three 100 mL flasks. Each of the above flasks was then added with 0.1 M HCl (5 mL), 0.1 M NaOH (5 mL) and 0.3% $H_2O_2$ solution (5 mL), respectively, added with methanol to a final volume of 20 mL and was subjected to ultrasonic extraction for 10 minutes.

Each sample was allowed to stand at room temperature for 24 hours and decomposed substances of tolterodine were quantitated by HPLC as follows.

[Analytical Method]
Test solution: tolterodine (~0.5 mg/mL)
Mobile phase: 45:55 mixture solution of ammonium dihydrogen phosphate and methanol, pH 7.0
HPLC condition: detector 220 nm, column ODS3 C-18

TABLE 1

Peak area ratio of decomposed substances of tolterodine under acidic/basic/oxidizing conditions

| Conditions | Total decomposed substances (%) |
|---|---|
| 0.1M HCl | 0.59 |
| 0.1M NaOH | 0.83 |
| 0.3% $H_2O_2$ | 4.74 |

Reference Example 2

Stress Decomposition Test of Tolterodine Under Heat Conditions

Tolterodine free base (25-30 mg) was weighed and added into four glass bottles which were then capped with plugs. Three of the glass bottles were placed in an oven preheated at 120° C. At 10 minutes, 20 minutes and 30 minutes, each glass bottle was taken out from the oven and was allowed to cool enough at room temperature. After adding methanol (100 mL) to the four glass bottles followed by ultrasonic extraction for 10 minutes, decomposed substances of tolterodine were quantitated by HPLC as in Reference Example 1.

TABLE 2

Peak area ratio of decomposed substances of tolterodine under heat conditions

| Conditions | Total decomposed substances (%) |
|---|---|
| 120° C./0 min | 0.45 |
| 120° C./10 min | 0.59 |
| 120° C./20 min | 0.63 |
| 120° C./30 min | 0.78 |

Test Example 1

Screening of Antioxidant

Tolterodine free base (500 mg) was mixed with ethanol (50 mL) in a 100 mL flask and 0.3% $H_2O_2$ solution was added thereto to a final volume of 100 mL.

Antioxidant, weighed 10 mg each, was added into two glass bottles. One bottle contained tolterodine and the antioxidant, while the other bottle contained only the antioxidant, which was prepared to exclude the peaks resulting from the decomposition of the antioxidant by $H_2O_2$.

Tolterodine solution (2 mL) or a 1:1 mixture solution of 0.3% $H_2O_2$ aqueous solution and ethanol (2 mL) were added to the two glass bottles containing the antioxidant. The bottles were agitated at 100 rpm and 25° C. for 2.5 days.

HPLC analysis was performed under the same condition as in Reference Example 1.

TABLE 3

Peak area ratio of decomposed substances of tolterodine

| Antioxidants | Total decomposed substances (%) |
|---|---|
| None | 26.08 |
| Lauryl gallate | 19.94 |
| n-Octyl gallate | 15.97 |

TABLE 3-continued

Peak area ratio of decomposed substances of tolterodine

| Antioxidants | Total decomposed substances (%) |
|---|---|
| Ethyl gallate | 13.00 |
| (+)-α-Tocopherol acetate | 23.56 |
| l-Ascorbic acid | 1.21 |
| l-Ascorbic acid 6-palmitate | 1.94 |
| Sodium thiosulfate | 1.94 |
| Sodium sulfite | 5.67 |
| l-Tartaric acid | 1.44 |
| l-Glutamic acid | 1.52 |
| Citric acid | 1.46 |
| d,l-Malic acid | 1.39 |
| Ethylenediaminetetraacetic acid calcium disodium salt | 29.69 |
| d,l-α-Tocopherol | 20.29 |
| l-Cysteine HCl | 1.70 |
| Butylated hydroxyanisole (BHA) | 23.87 |
| Butylated hydroxytoluene (BHT) | 18.82 |

Test Example 2

Preparation of Gels Comprising Antioxidants and Evaluation of Stability

Gels for transdermal administration were prepared using l-ascorbic acid, l-ascorbic acid 6-palmitate, sodium thiosulfate, l-tartaric acid, l-glutamic acid, citric acid, d,l-malic acid or l-cysteine HCl, which exhibited significantly reduced (less than 2%) production of decomposed substances in Test Example 1.

Hydroxypropyl cellulose, ethanol and purified water were weighed into a vial and stirred to prepare a transparent solution. Then, tolterodine and the antioxidant were weighed into the solution and stirred to prepare a gel. Entire procedure was carried out inside a nitrogen chamber.

TABLE 4

| Unit (g) | Ex. 1 | Ex. 2 | Ex. 3 | Ex. 4 | Ex. 5 | Ex. 6 | Ex. 7 | Ex. 8 |
|---|---|---|---|---|---|---|---|---|
| Tolterodine | 1.32 | 1.32 | 1.32 | 1.32 | 1.32 | 1.32 | 1.32 | 1.32 |
| Ethanol | 2 | 2 | 2 | 2 | 2 | 2 | 2 | 2 |
| Purified water | 4 | 4 | 4 | 4 | 4 | 4 | 4 | 4 |
| Propylene glycol | 1.5 | 1.5 | 1.5 | 1.5 | 1.5 | 1.5 | 1.5 | 1.5 |
| l-Ascorbic acid | 0.1 | — | — | — | — | — | — | — |
| l-Ascorbic acid 6-palmitate | — | 0.1 | — | — | — | — | — | — |
| Sodium thiosulfate | — | — | 0.1 | — | — | — | — | — |
| l-Tartaric acid | — | — | — | 0.1 | — | — | — | — |
| l-Glutamic acid | — | — | — | — | 0.1 | — | — | — |
| Citric acid | — | — | — | — | — | 0.1 | — | — |
| d,l-Malic acid | — | — | — | — | — | — | 0.1 | — |
| l-Cysteine HCl | — | — | — | — | — | — | — | 0.1 |
| Hydroxypropyl cellulose | 0.5 | 0.5 | 0.5 | 0.5 | 0.5 | 0.5 | 0.5 | 0.5 |

The prepared gels were stored under an accelerated condition (40° C., 75% RH) for 3 weeks. After adding methanol to adjust volume followed by ultrasonic extraction, decomposed substances of tolterodine were quantitated as in Reference Example 1.

TABLE 5

Peak area ratio of decomposed substances of tolterodine

| | Total decomposed substances (%) |
|---|---|
| Example 1 | 0.68 |
| Example 3 | 0.88 |
| Example 5 | 0.75 |
| Example 8 | 0.92 |

Test Example 3

Preparation of Patches Comprising Antioxidants and Evaluation of Stability

Tolterodine, ethanol and the antioxidant were weighed and then added into a vial. After adding an acrylic adhesive, the mixture was stirred for about 10 minutes. After allowing to stand at room temperature for at least 4 hours to remove the gas included in the solution, the solution was applied on a polyester film to a thickness of 400 μm using an applicator at a rate of 0.5 m/min. Then, after drying in a convection dryer at 50° C. for 50 minutes, followed by lamination of a backing layer (B/L) and cutting into patches using a 30 cm² cutter, the resultant patch was packaged in aluminum pouches and stored under an accelerated condition (40° C., 75% RH).

TABLE 6

| | Unit (g/vial) | Comp. Ex. 1 | Ex. 9 | Ex. 10 | Ex. 11 |
|---|---|---|---|---|---|
| Drug | Tolterodine | 1.32 | 1.32 | 1.32 | 1.32 |
| Solvent | Ethanol | 1 | 1 | 1 | 1 |
| Antioxidant | l-Ascorbic acid 6-palmitate | — | 0.1 | 0.2 | 0.4 |
| Adhesive | Acrylic adhesive | 16.24 | 16.24 | 16.24 | 16.24 |
| Application thickness (μm) | | 400 | 400 | 400 | 400 |

On 1st, 2nd, 3rd and 4th weeks, the patches were subjected to quantification of decomposed substances of tolterodine by HPLC. Each patch was cut finely and subjected to ultrasonic extraction after adjusting volume with ethyl acetate. Then, after adjusting volume with methanol, analysis was performed as in Reference Example 1.

TABLE 7

Peak area ratio of decomposed substances of tolterodine

| | Storage period | Total decomposed substances (%) |
|---|---|---|
| Comparative Example 1 | 0 week | 0.45 |
| | 1 week | 0.98 |
| | 2 weeks | 1.36 |
| | 3 weeks | 1.73 |
| Example 9 | 0 week | 0.23 |
| | 1 week | 0.45 |
| | 2 weeks | 0.61 |
| | 3 weeks | 0.93 |
| Example 10 | 0 week | 0.15 |
| | 1 week | 0.40 |
| | 2 weeks | 0.53 |
| | 3 weeks | 0.80 |
| Example 11 | 0 week | 0.35 |
| | 1 week | 0.48 |
| | 2 weeks | 0.63 |
| | 3 weeks | 0.83 |

As shown in Table 7, the addition of l-ascorbic acid 6-palmitate to the patch resulted in about 50% less production of decomposed substances after storage for 3 weeks as compared to the patch not comprising l-ascorbic acid 6-palmitate.

While the present invention has been described with respect to the specific embodiments, it will be apparent to those skilled in the art that various changes and modifications may be made without departing from the spirit and scope of the invention as defined in the following claims.

The invention claimed is:

1. A transdermal composition comprising (1) tolterodine and (2) a stabilizer, wherein the stabilizer is an organic acid, an amino acid, a metal thiolate, or a combination thereof and wherein less than 2% of the tolterodine in a solution of tolterodine and the stabilizer decomposes after 2.5 days at 25° C., wherein the stabilizer is contained in an amount of 1 to 40 parts by weight based on 100 parts by weight of tolterodine.

2. The composition according to claim 1, wherein the organic acid is selected from formic acid, fumaric acid, malic acid, succinic acid, acetic acid, palmitic acid, tartaric acid, ascorbic acid, uric acid, sulfonic acid, sulfinic acid, aspartic acid, citric acid, isocitric acid, α-ketoglutaric acid and glutamic acid.

3. The composition according to claim 1, wherein the amino acid, is selected from glutamine, asparagine, serine, threonine, tyrosine, cysteine and cystine.

4. The composition according to claim 1, wherein the metal thiolate is selected from sodium thiosulfate, potassium thiosulfate and magnesium thiosulfate.

5. The composition according to claim 1, which is formulated into a gel or a patch.

6. The composition according to claim 2, which is formulated into a gel or a patch.

7. The composition according to claim 3, which is formulated into a gel or a patch.

8. The composition according to claim 4, which is formulated into a gel or a patch.

9. The composition according to claim 1, which does not contain any urea-containing compound.

10. A transdermal composition comprising (1) tolterodine and (2) a stabilizer, wherein the stabilizer is an organic acid, an amino acid, a metal thiolate, or a combination thereof and wherein less than 2% of the tolterodine in a solution of tolterodine and the stabilizer decomposes after 2.5 days at 25° C., and wherein the organic acid is selected from malic acid, palmitic acid, tartaric acid, ascorbic acid, sulfinic acid, citric acid, isocitric acid, and glutamic acid; wherein the amino acid is selected from glutamine, asparagine, serine, threonine, and tyrosine; and wherein the metal thiolate is selected from sodium thiosulfate, potassium thiosulfate, and magnesium thiosulfate, and wherein the stabilizer is contained in an amount of 1 to 40 parts by weight based on 100 parts by weight of tolterodine.

11. The composition according to claim 10, which is formulated into a gel or a patch.

12. A transdermal composition comprising (1) tolterodine and (2) a stabilizer, wherein the stabilizer is an organic acid, an amino acid, a metal thiolate, or a combination thereof and wherein less than 2% of the tolterodine in a solution of tolterodine and the stabilizer decomposes after 2.5 days at 25° C., and wherein the metal thiolate is selected from sodium thiosulfate, potassium thiosulfate and magnesium thiosulfate.

13. The composition according to claim 12, wherein the stabilizer is contained in an amount of 1 to 40 parts by weight based on 100 parts by weight of tolterodine.

14. The composition according to claim 12, which is formulated into a gel or a patch.

\* \* \* \* \*